United States Patent
Dijksman et al.

(10) Patent No.: US 9,878,094 B2
(45) Date of Patent: Jan. 30, 2018

(54) MEDICAMENT DELIVERY DEVICE, CAPSULE AND IN VIVO MEDICINE DELIVERY OR DIAGNOSTIC SYSTEM

(75) Inventors: Johan Frederik Dijksman, Weert (NL); Frits Tobi De Jongh, Beek en Donk (NL); Michel Gerardus Pardoel, Mierlo (NL); Anke Pierik, Eindhoven (NL); Judith Margreet Rensen, Eindhoven (NL); Jeff Shimizu, Cortlandt Manor, NY (US); Hans Zou, Windsor, NJ (US); Remus Albu, Forest Hills, NY (US); Ventzeslav Iordanov, Valkenswaard (NL); Hans Marc Bert Boeve, Hechtel-Eksel (BE)

(73) Assignee: STOCO 10 GMBH, Heilbronn (DE)

( * ) Notice: Subject to any disclaimer, the term of this patent is extended or adjusted under 35 U.S.C. 154(b) by 519 days.

(21) Appl. No.: 12/515,383

(22) PCT Filed: Nov. 6, 2007

(86) PCT No.: PCT/IB2007/054491
§ 371 (c)(1),
(2), (4) Date: May 18, 2009

(87) PCT Pub. No.: WO2008/062335
PCT Pub. Date: May 29, 2008

(65) Prior Publication Data
US 2010/0056874 A1    Mar. 4, 2010

Related U.S. Application Data

(60) Provisional application No. 60/866,641, filed on Nov. 21, 2006.

(51) Int. Cl.
*A61M 31/00* (2006.01)
*A61B 5/00* (2006.01)
(Continued)

(52) U.S. Cl.
CPC ......... *A61M 5/14593* (2013.01); *A61B 5/073* (2013.01); *A61B 5/14539* (2013.01);
(Continued)

(58) Field of Classification Search
CPC ...... A61M 5/14593; A61M 2205/3561; A61M 5/14276; A61M 31/002;
(Continued)

(56) References Cited

U.S. PATENT DOCUMENTS 3,631,847 A * 1/1972 Hobbs, II ........... A61B 5/02755
600/432
3,923,060 A * 12/1975 Ellinwood, Jr. ........... 604/891.1
(Continued)

FOREIGN PATENT DOCUMENTS

EP    0781567    7/1997
JP    5228128    7/1993
(Continued)

OTHER PUBLICATIONS

Translated Japanese Office Actoin dated May 28, 2013 for Japanese patent application No. 2009536827, counterpart foreign application of U.S. Appl. No. 12/515,383, 8 pages.
(Continued)

*Primary Examiner* — Nathan R Price
*Assistant Examiner* — Justin L Zamory
(74) *Attorney, Agent, or Firm* — Emerson Thomson Bennett, LLC; Roger D. Emerson

(57) ABSTRACT

A medicament delivery device, which comprises a driving mechanism and a housing (1) having a reservoir (2), which is at least partly filled with a substance and which is sealed at least on one side with a flexible wall (21). The driving mechanism is adapted to press a piston (23) against the flexible wall (21) thereby releasing the substance from the reservoir (2) through an opening (25) in the reservoir (2).
(Continued)

This provides for a safe and reliable medicament delivery device.

17 Claims, 3 Drawing Sheets

(51) Int. Cl.
    *A61M 5/145* (2006.01)
    *A61B 5/07* (2006.01)
    *A61B 5/145* (2006.01)
    *A61B 1/04* (2006.01)
    *A61B 5/01* (2006.01)
    *A61M 5/142* (2006.01)

(52) U.S. Cl.
    CPC ............ *A61B 5/4839* (2013.01); *A61B 1/041* (2013.01); *A61B 5/01* (2013.01); *A61M 5/14276* (2013.01); *A61M 31/002* (2013.01); *A61M 2005/14204* (2013.01); *A61M 2205/3561* (2013.01)

(58) Field of Classification Search
    CPC ........ A61M 2005/14204; A61M 31/00; A61M 2210/1053; A61M 5/14224; A61M 5/14586; A61M 5/145; A61B 5/073; A61B 5/14539; A61B 5/4839; A61B 1/041; A61B 5/01
    USPC ...... 604/890.1, 891.1, 892.1, 93.01, 110, 20, 604/300, 135, 145; 424/9.1
    See application file for complete search history.

(56) References Cited

U.S. PATENT DOCUMENTS

| | | | |
|---|---|---|---|
| 4,425,117 A * | 1/1984 | Hugemann et al. ......... 604/244 |
| 4,439,197 A * | 3/1984 | Honda et al. ............. 604/891.1 |
| 4,447,224 A * | 5/1984 | DeCant et al. .............. 604/67 |
| 4,457,752 A * | 7/1984 | Vadasz ...................... 604/135 |
| 5,034,004 A * | 7/1991 | Crankshaw ......... A61M 5/1452 128/DIG. 1 |
| 5,279,607 A | 1/1994 | Schentag et al. |
| 5,527,288 A * | 6/1996 | Gross et al. ................. 604/140 |
| 5,848,991 A | 12/1998 | Gross et al. |
| 5,858,001 A * | 1/1999 | Tsals ................. A61M 5/14248 604/135 |
| 6,153,213 A * | 11/2000 | Porter .................. A61K 9/0068 424/438 |
| 6,485,471 B1 * | 11/2002 | Zivitz ................. A61M 5/1452 604/181 |
| 2003/0136189 A1 | 7/2003 | Lauman |
| 2003/0199855 A1 * | 10/2003 | Rogers et al. ............ 604/891.1 |
| 2004/0092873 A1 * | 5/2004 | Moberg ..................... 604/131 |
| 2004/0133166 A1 | 7/2004 | Moberg |
| 2004/0253304 A1 | 12/2004 | Gross |
| 2005/0075559 A1 | 4/2005 | Houzego |
| 2006/0259015 A1 * | 11/2006 | Steinbach ................. 604/891.1 |
| 2009/0306633 A1 * | 12/2009 | Trovato et al. ........... 604/891.1 |

FOREIGN PATENT DOCUMENTS

| | | |
|---|---|---|
| JP | 2002528676 | 9/2002 |
| WO | WO8902286 | 3/1989 |
| WO | 2003018089 A1 | 3/2003 |
| WO | 2006 077 528 | 7/2006 |
| WO | 2008 012 700 | 1/2008 |

OTHER PUBLICATIONS

The European Office Action dated Feb. 6, 2014 for European patent application No. 07826981.8, a counterpart foreign application of U.S. Appl. No. 12/515,383, 4 pages.

Translated Japanese Office Action dated Dec. 3, 2013 for Japanese patent application No. 2009-536827, a counterpart foreign application of U.S. Appl. No. 12/515,383, 6 pages.

Translated Japanese Office Action dated Jun. 10, 2014 for Japanese patent application No. 2009-536827, a counterpart foreign application of U.S. Appl. No. 12/515,383, 4 pages.

* cited by examiner

MEDICAMENT DELIVERY DEVICE, CAPSULE AND IN VIVO MEDICINE DELIVERY OR DIAGNOSTIC SYSTEM

The invention relates to a medicament delivery device, comprising a housing having a driving mechanism and a reservoir, which is at least partly filled with a substance and which is sealed at least on one side with a flexible wall. The invention also relates to a capsule for introduction into a bodily lumen comprising a medicament delivery device. The invention further relates to an in vivo medicine delivery or diagnostic system.

Capsules or pills for introduction into a bodily lumen are known and for example used for medicament release and for diagnosis of the gastrointestinal (GI) tract in the human or animal body. Electronic pills for medicament release typically have a housing made from bio-compatible materials that houses both a medicament reservoir containing a pre-dosed amount of a medicament and control electronics for precisely delivering the medicament to a pre-selected site in the GI tract of a human or animal. Also contained by the housing is a means for providing a link for wireless communication by the pill to the outside of the body upon ingestion of the pill by a subject. The electronics enable the pill to deliver the on board medicament at a specific site in the GI tract of a human or animal using sensors, timing or location. A capsule or pill for diagnosis of the GI track typically comprises a sensor (and typically not a medicine reservoir) that monitors a body temperature or a pH value, and/or comprises an image sensor that is arranged to create images of the GI tract.

US 2004/0253304 A1 discloses a capsule with a medicament delivery device that includes a substance, for example a drug, stored by the capsule in a reservoir and a driving mechanism that, in response to a change of state of an environmentally-sensitive mechanism, is adapted to drive the substance into the GI tract. The driving mechanism comprises a movable member, such as a membrane, which moves within the capsule in response to the generation of gas by a generator. The generated or released gas produces an increased pressure on the membrane. The pressure loaded membrane, in turn, applies pressure to the substance, thereby driving the substance out of the medicine reservoir into the GI tract. In other configurations of the medicament delivery device the movable member comprises a piston. In yet other configurations of the medicament delivery device a movable member is not provided, but instead a gas generator acts directly on the substance.

A disadvantage of the known medicament delivery device is that the gas generator in the capsule produces gas with a relatively high pressure. The temporarily increased pressure in the capsule results in a safety hazard and a less reliable medicament delivery device.

It is an object of the invention to provide a medicament delivery device, which is more reliable and safer. The invention is defined by the independent claims. Advantageous embodiments are defined by the dependent claims.

This object is achieved by the medicament delivery device according to the invention, which is characterized in that the drive mechanism is adapted to press a piston against the flexible wall thereby releasing the substance from the reservoir through an opening. Because of the piston pressing against the flexible wall, there is no need for a gas with a high pressure inside the capsule and therefore the safety and reliability of the medicament delivery device are both increased. Another advantage is that the piston does not need to fit tightly inside the housing, because the flexible wall, and not the piston, seals the medicine reservoir. The piston in this invention is not a hermetically sealed barrier for the substance, instead, the flexible wall serves that function, and the piston functions as a driving element that releases the substance from the reservoir. As the wall is flexible, it follows the movement of the piston, which presses against the flexible wall, until at least part of the substance is released.

This object is also achieved by the capsule for introduction into a bodily lumen comprising the medicament delivery device according to the invention and electronic circuitry to control the piston. This object is also achieved by the in vivo medicine delivery or diagnostic system comprising a capsule having the medicament delivery device according to the invention and an external device arranged to communicate with the electronic circuitry. In an embodiment of the capsule according to the invention, the housing comprises a first part and a second part, in which the first part of the housing is secured to the second part of the housing thereby clamping the flexible wall in between the first part of the housing and the second part of the housing and separating the drive mechanism from the reservoir. In this way the substance stored in the reservoir is sealed from the drive mechanism.

In a further embodiment of the capsule according to the invention, the first part of the housing comprises a protrusion and the second part of the housing comprises a recess, in which the flexible wall is clamped in between the first part of the housing and the second part of the housing by insertion of the protrusion into the recess thereby securing the first part of the housing to the second part of the housing. In this way the sealing length of the flexible wall is enlarged, which increases the sealing strength of the flexible wall and hence the reliability of the device.

In an embodiment of the capsule according to the invention, the piston is provided with a threaded hole and is driven by a threaded component of the drive mechanism, which threaded component is mounted onto an electrical motor. The combination of the threaded hole in the piston and the threaded component mounted onto the electrical motor advantageously provides for a simple and well-known drive mechanism.

In an embodiment of the capsule according to the invention, a part of a surface of the piston that contacts the flexible wall during release of the substance from the reservoir comprises a low friction material. This advantageously reduces friction between the piston and the flexible wall resulting in an improved adaptation of the flexible wall to the surface of the piston.

These and other aspects of the invention will be further elucidated and described with reference to the drawings, in which.

The Figures are not drawn to scale. In general, identical components are denoted by the same reference numerals in the figures.

Implementations of a medicament delivery device according to the invention provided in a capsule will be explained below as an example. However, the invention is not limited to these examples and may also be applied in other medicament delivery devices.

Figure 1:
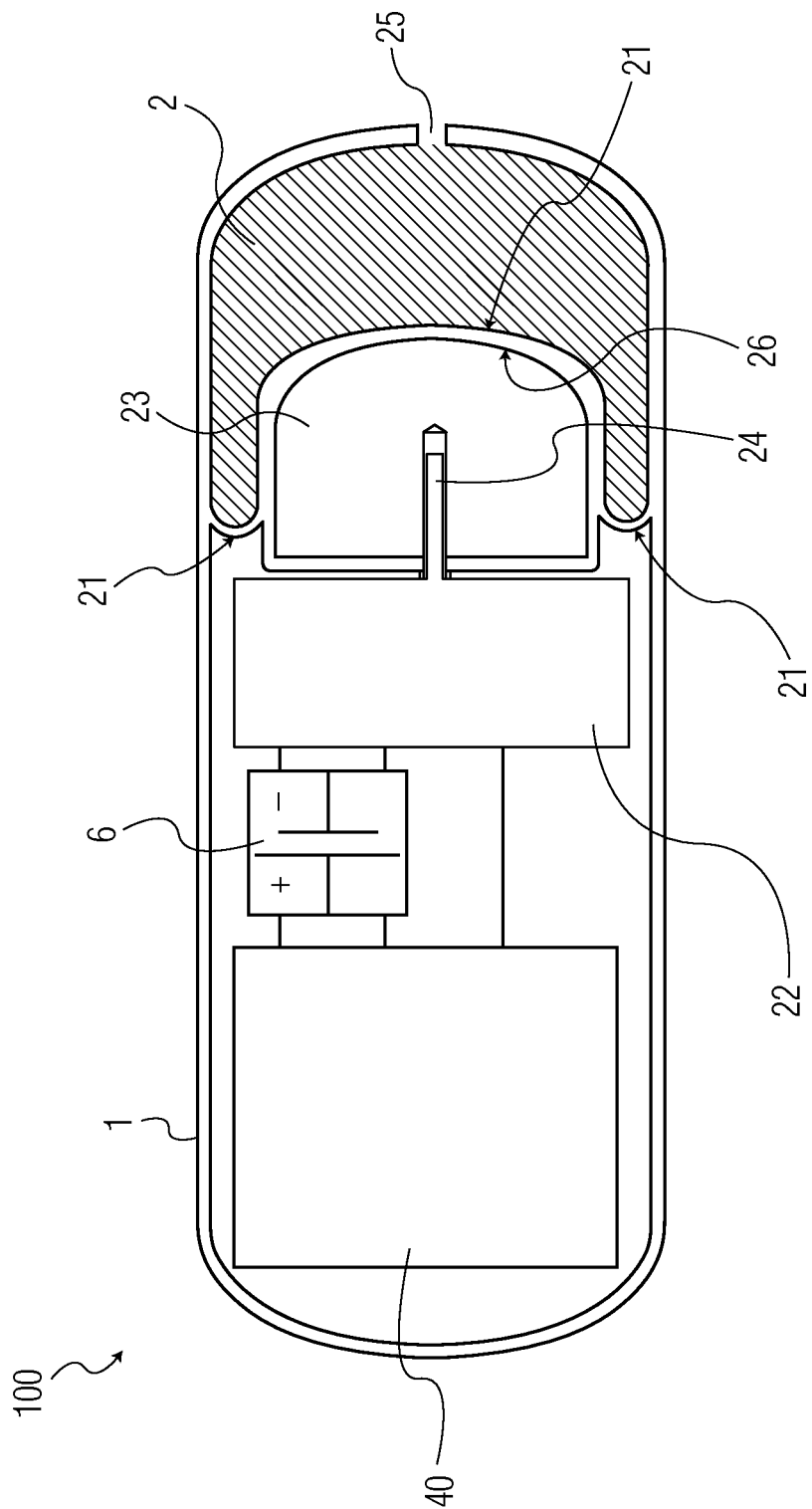
FIG. 1 is schematic cross-sectional view of an embodiment of a capsule having a medicament delivery device according to the invention.

FIG. 1 is a schematic cross-sectional view of a capsule 100, which is a self-contained, electronically controlled medicament delivery system for use by a subject, human or animal, for example by ingestion. The capsule 100 comprises a cylindrical housing 1 in which, amongst others, electronic control circuitry 40, a medicament delivery device and sensors for diagnostic purposes are mounted. Housing 1 is preferably made from bio-compatible materials such that capsule 100 is bio-compatible for at least the amount of time it requires to traverse the GI tract of a human or animal. The bio-compatible materials are preferably stable at room temperature and below room temperature, such that capsule 100 has a long shelf life. Housing 1 may be fabricated from a biologically safe polymeric material such as, for example, polytetrafluoroethylene, polypropylene, polyethylene, acrylics and the like. Housing 1 is more preferably manufactured from materials used to fabricate implantable devices, including pacemaker leads and cardiac prosthesis devices, such as artificial hearts, heart valves, intra-aortic balloons, and ventricular assist devices. Assembled capsule 100 is preferably sized to be suitable to be swallowed by a human or animal. Preferably, assembled capsule 100 is about 1 cm in diameter and 2 to 3 cm long.

A power source 6 powers the electronic control circuitry 40 in order for the medicament delivery device and sensors for diagnostic purposes to operate. Power source 6 additionally powers any other electrically powered equipment housed by capsule 100. Power source 6 may be a battery, a capacitor or any other known means for providing a power supply.

The electronic control circuitry 40 is, for example, used for communication and for controlling release of a substance stored in a reservoir 2 and may include, without limitation, a drive unit for an electrical motor, a microprocessor, sensors for aiding in determining the location of capsule 100 without physical contact, a temperature sensor, an image sensor, communication means such as, for example, an RF transceiver and an antenna. The RF transceiver provides for an RF link and is used for transmitting signals to and receiving signals from outside of the capsule 100. For example, the transceiver communicates with a portable device (not shown), which is able to program a medicament release profile by transmitting a signal that is subsequently received by the transceiver. The portable device may also communicate with a base station (not shown) with, for example, an infrared link, which base station is used for communication with, for example, a medical expert. For a long shelf life it is essential that the electronic control circuitry 40 is completely decoupled from the power source 6, otherwise a small leakage current will ultimately empty the power source 6. To start the electronic circuitry, it must be waked-up, and for that purpose a wake-up circuit (not shown) may be designed that is powered from the outside by inductive radiation that is received by an antenna integrated in the capsule 100.

The electronic control circuitry 40 comprises a large number of electronic components that need to be mutually electrically connected. For this purpose, one continuous flex foil is applied to provide for a printed circuit board on which various electronic components are attached. The attachment of various electronic components on the flex foil and the integration of electrical connections between the electronic components on the flex foil 1 reduces the number of components and hence increases the reliability of the capsule 100.

The reservoir 2 is used for storing a substance that can be delivered to the GI tract inside the human body via a dispensing hole 25 in, for example, the housing 1. The substance may refer to, for example, medicines, non-medicinal substances, contrast agents, radiological agents and imaging markers. In this embodiment the substance is preferably a medicament for treatment of diseases of the GI tract. The dispensing hole 25 may comprise a removable seal or plug, which, for example, comprises a material that dissolves in the GI tract in the human or animal body thereby opening the dispensing hole 25. The medicament delivery device further comprises a movable piston 23, which is driven by, for example, an electrical (stepper) motor 22 controlled by the electronic control circuitry 40. The motor 22, for example, translates the piston 23 via a screw mechanism 24 towards the dispensing hole 25. In another embodiment the motor 22 is a linear motor directly driving the piston 23 towards the dispensing hole 25.

The reservoir 2 is on one side sealed with a flexible wall 21, which is attached to the housing 1. A part of a surface 26 of the piston 23 is pressed against the flexible wall 21, and a part of the flexible wall 21 contacts a part of the surface 26 of the piston 23 and is adjusted to the shape of the contacting part of the surface 26 of the piston 23. In order to prevent the piston 23 from rotation, the piston 23 is, for example, provided with a notch that runs into a track that is provided in the housing 1 (not shown). The piston 23 is moved via the motor 22 towards the dispensing hole 25. When the piston 23 contacts and presses against the flexible wall 21, the flexible wall 21 presses against the substance in the reservoir 2, and, as a result, the substance is released from the reservoir 2 through the dispensing hole 25.

Because the flexible wall 21 seals the substance in the reservoir 2, the piston 23 is only used to press the substance from the reservoir 2 through the dispensing hole 25. The piston 23 has no sealing function, which sealing function is normally attributed to pistons in general. Because the piston 23 does not form a seal for the substance in the reservoir 2, there is no tight tolerance requirement for fitting the piston 23 into the housing 1. In fact, the piston 23 even does not need to contact the inside surface of the housing 1 to provide for a proper release of the substance from the reservoir 2. The surface 26 of the piston 23 may be provided with a material that has a low friction, such as for example Teflon™. In this way the flexible wall 21 that contacts the contact surface 26 is able to glide over the surface 26 of the piston 23 with a relatively low friction and the flexible wall 21 will fold in an optimum way in the space between the piston 23 and the housing 1.

The flexible wall 21 is made of a material that provides for a sealing of the reservoir 2 and has flexible properties that allow for adjusting to the shape of the surface 26 of the piston 23 without tearing apart or damaging the flexible wall. Such a material may be, for example, polymer based laminates like a pharmaceutical grade Polyethylene/Polychlorotrifluoroethylene (PE/PCTFE) flexible film.

Figure 2:
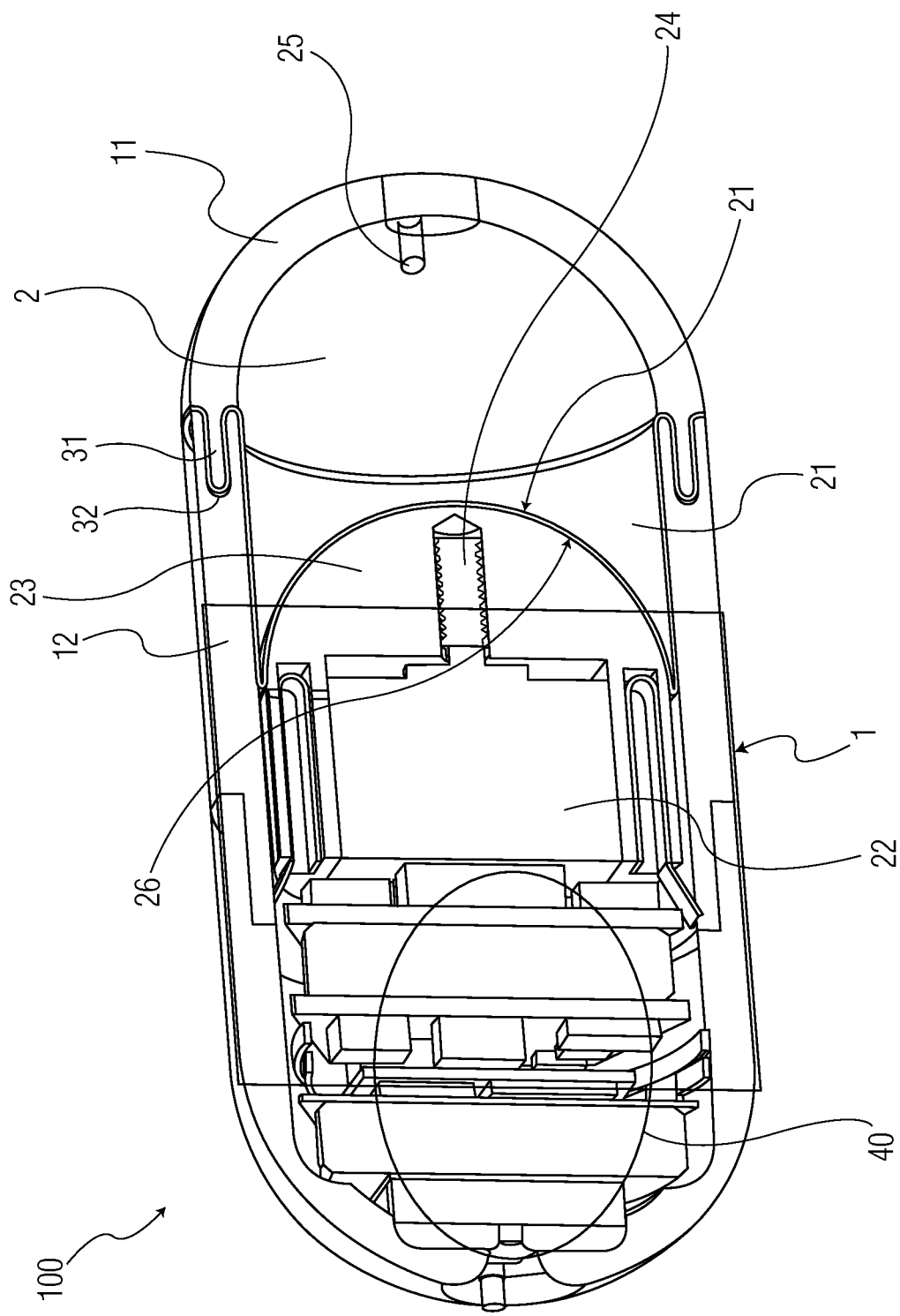
FIG. 2 is a perspective cross-sectional view of an embodiment of a capsule having a medicament delivery device according to the invention.
Figure 3:
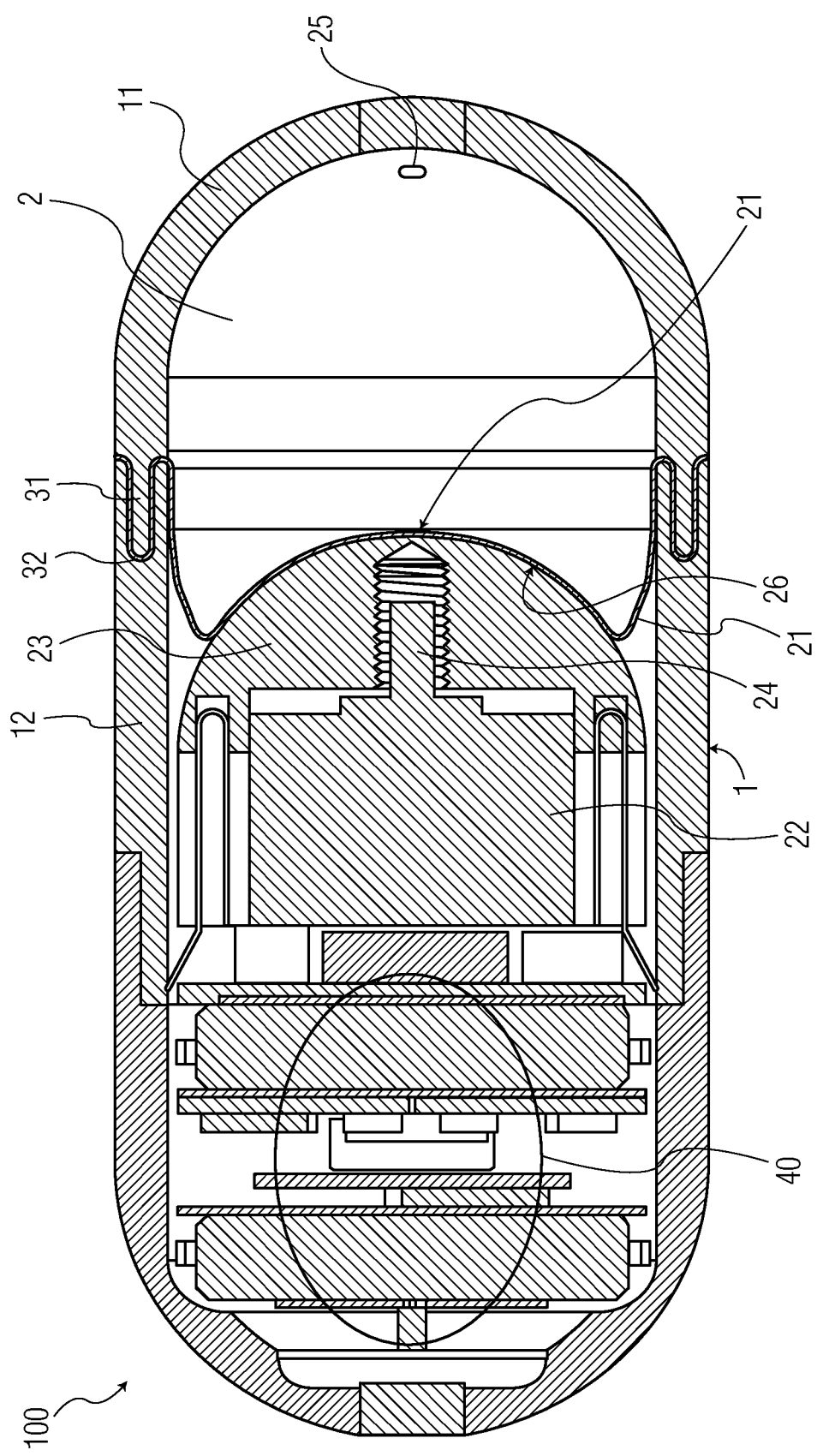
FIG. 3 is a cross-sectional view of an embodiment of a capsule having a medicament delivery device according to the invention.

FIG. 2 shows a perspective cross-sectional view of the capsule 100 having a medicament delivery device according to the invention and FIG. 3 is a cross-sectional view of the capsule 100 having a medicament delivery device according to the invention, and the electronic control circuitry 40, having several different components, the motor 22 which drives the piston 23 via the screw mechanism 24 towards the dispensing hole 25 such that the surface 26 of the piston 23 is pressed against the flexible wall 21. A first part 11 of the housing 1 is secured to a second part 12 of the housing 1 by the insertion of a protrusion 31 of the first part 11 into a recess 32 of the second part 12. In between the protrusion 31 and the recess 32 a part of the flexible wall 21 is clamped providing for a fixation of the flexible wall 21. In this way the flexible wall 21 seals the substance that is in the reservoir 2 and thus forms a barrier between the substance and the remaining components of the medicament delivery device and capsule 100. In order to enhance the sealing properties of the flexible wall 21, biocompatible adhesives may be used for the adhesion of the flexible wall 21 in between the protrusion 31 and the recess 32, or, alternatively, ultrasonic frictional heating may be applied. Note that the first part 11 of the housing 1 comprises the reservoir 2 and that the second part 12 of the housing 2, comprising the remaining components of the medicament delivery device and capsule 100, is separated from the reservoir 2 by the flexible wall 21. The protrusion 31 and the recess 32 provide for an increased length over which the flexible wall 21 is clamped between the first part 11 and the second part 12 of the housing 1, thereby increasing the sealing strength of the flexible wall 21 and minimizing leakage of the substance to the outside of the reservoir 2.

The flex foil, on which various electronic components are attached, is electrically and mechanically attached to the motor 22.

In summary, the invention provides for a medicament delivery device, which comprises a driving mechanism and a housing having a reservoir, which is at least partly filled with a substance and which is sealed at least on one side with a flexible wall. The driving mechanism is adapted to press a piston against the flexible wall thereby releasing the substance from the reservoir through an opening in the reservoir. This provides for a safe and reliable medicament delivery device.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention claimed is:

1. A medicament delivery device, comprising:
   a housing configured for ingestion by a patient and comprising a first part and a second part secured to the first part, an inner surface of the first part and an inner surface of the second part defining an interior volume of the housing; a flexible wall having an outer periphery, wherein:
   the flexible wall is secured between the first part and the second part proximate the outer periphery such that, proximate the outer periphery, the flexible wall is fixed relative to the first part and the second part, the flexible wall separates the interior volume of the housing into a first compartment defined by the first part of the housing and the flexible wall and a second compartment defined by the second part of the housing and the flexible wall, and the flexible wall seals the first compartment of the interior volume relative to the second compartment of the interior volume; a reservoir disposed in the first compartment of the interior volume of the housing; a piston disposed in the second compartment of the interior volume of the housing; and
   a driving mechanism disposed in the second compartment of the interior volume of the housing, configured to press the piston against the flexible wall to cause the substance to be released from the reservoir through an opening into a gastrointestinal tract of the patient.

2. The medicament delivery device according to claim 1, wherein the first part of the housing comprises one of a protrusion or a recess and the second part of the housing comprises the other of the protrusion and the recess, in which the flexible wall is clamped in between the first part of the housing and the second part of the housing by insertion of the protrusion into the recess thereby securing the first part of the housing to the second part of the housing.

3. The medicament delivery device according to claim 1, wherein the driving mechanism comprises a threaded component mounted on an electric motor, and the piston is driven by the threaded component of the driving mechanism.

4. The medicament delivery device according to claim 1, wherein a part of a surface of the piston that contacts the flexible wall during release of the substance from the reservoir comprises a low friction material.

5. A capsule for introduction into a bodily lumen comprising:
   a medicament delivery device according to claim 1; and electronic circuitry to control the piston.

6. In vivo medicament delivery or diagnostic system comprising:
   a capsule according to claim 5; and an external device arranged to communicate with the electronic circuitry in the capsule.

7. A medicament delivery device for delivering a substance inside a body, the device comprising:
   a housing configured as an elongate capsule comprising a sidewall formed about a longitudinal axis, the sidewall having a diameter smaller than a length measured along the longitudinal axis of the capsule, the capsule adapted for complete insertion into a user's body and defining a dispensing hole, the housing comprising a first part and a
   second part secured to the first part, the first part comprising a first portion of the sidewall and the second part comprising a second portion of the sidewall; a flexible wall secured between the first portion of the sidewall and the second portion of the sidewall proximate an outer periphery of the flexible wall such that the outer periphery of the flexible wall is fixed relative to the first part and the second part, the
   flexible wall extending across the entirety of an inner diameter of the housing to separate the housing into a first compartment and a second compartment and forming a seal between the first compartment and the second compartment, the first compartment comprising a reservoir formed by a portion of the housing including the dispensing hole and the flexible wall; and
   a driving mechanism disposed in the second compartment to displace the flexible wall toward the first compartment, causing at least a portion of the substance to be released from the reservoir through the dispensing hole, wherein the driving mechanism comprises an actuatable piston adapted to press against the flexible wall.

8. The device according to claim 7, wherein the driving mechanism comprises a stepper motor and a screw mechanism, the stepper motor being configured to drive the piston to press against the flexible wall via the screw mechanism.

9. The device according to claim 7, wherein the driving mechanism comprises a linear motor configured to directly drive the piston to press against the flexible wall.

10. The device according to claim 7, wherein the piston has no sealing function with respect to the reservoir.

11. The device according to claim 7, wherein the first part comprises one of a protrusion or a recess and the second part comprises the other of the protrusion or the recess wherein the recess is configured to receive the protrusion to secure the first part to the second part, and wherein the flexible wall is damped between the protrusion and the recess.

12. A capsule for delivering a substance inside a body, the capsule comprising:
   a housing comprising a first part and a second part secured to the first part, the housing comprising a sidewall extending between opposite ends defining an internal volume and configured as a generally elongate capsule for complete insertion into a bodily lumen, the elongate capsule having a length along a longitudinal axis greater than a diameter of the capsule, normal the longitudinal axis, and the internal volume having an internal circumference normal to the longitudinal axis;
   a flexible wall in the housing having an outer circumference conforming to the internal circumference of the internal volume of the housing, the flexible wall being secured, proximate the outer circumference, between the first part of the housing and the second part of the housing at the sidewall such that the flexible wall is fixed relative to the first part and the second, part proximate the sidewall, the flexible wail completely partitioning the internal volume of the capsule into a first compartment comprising a reservoir on a first side of the flexible wall, along the longitudinal axis, and a second compartment on a second side of the flexible wall, along the longitudinal axis, and the flexible wall sealing the first compartment relative to the second compartment; a driving mechanism disposed in the second compartment and configured to press against the flexible wall, causing the flexible wall to displace in a direction toward the reservoir to reduce a volume of the reservoir; control circuitry disposed in the second compartment and configured to operate the driving mechanism, and
   a power source disposed in the second compartment fbr providing power to at least one of the control circuitry and the driving mechanism.

13. The medicament delivery device of claim 7, wherein the housing is configured as an ingestible capsule.

14. The capsule of claim 12, wherein the housing is configured as an ingestible capsule.

15. The medicament delivery device of claim 1, wherein the piston is not sealed relative to a sidewall of the capsule.

16. The capsule of claim 12, wherein the driving mechanism comprises an actuatable piston.

17. A method comprising:
   causing a patient to ingest the medicament delivery device of claim 1.

* * * * *